United States Patent [19]

Frank et al.

[11] Patent Number: 4,598,058

[45] Date of Patent: Jul. 1, 1986

[54] MOLDED CATALYST MATERIALS CONTAINING REDUCED COBALT AND/OR NICKEL PARTICLES

[75] Inventors: Gerhard Frank, Hirschberg; Gerald Neubauer, Weinheim; Paul Duffner, Ludwigshafen; Hans J. Wilfinger, Schifferstadt, all of Fed. Rep. of Germany

[73] Assignee: BASF Aktiengesellschaft, Fed. Rep. of Germany

[21] Appl. No.: 696,792

[22] Filed: Jan. 31, 1985

[30] Foreign Application Priority Data

Feb. 1, 1984 [DE] Fed. Rep. of Germany ....... 3403377

[51] Int. Cl.⁴ .................. B01J 23/78; B01J 23/74; B01J 27/185; C07C 85/12
[52] U.S. Cl. .................... 502/183; 260/690; 502/184; 502/185; 502/213; 502/243; 502/252; 564/490; 564/492; 568/814; 568/864; 568/881
[58] Field of Search ................ 502/183-185, 502/213, 338

[56] References Cited

U.S. PATENT DOCUMENTS

| | | | |
|---|---|---|---|
| 3,232,888 | 2/1966 | Adam | 252/435 |
| 3,344,085 | 9/1967 | Isacks et al. | 502/185 |
| 4,480,051 | 10/1984 | Wu | 502/338 |
| 4,521,527 | 6/1985 | Frank et al. | 502/184 |

FOREIGN PATENT DOCUMENTS

| | | |
|---|---|---|
| 1072972 | 7/1960 | Fed. Rep. of Germany . |
| 1259899 | 8/1968 | Fed. Rep. of Germany . |
| 2654028 | 1/1976 | Fed. Rep. of Germany . |
| 1407414 | 12/1965 | France . |
| 1059989 | 2/1967 | United Kingdom . |
| 1143390 | 2/1969 | United Kingdom . |
| 1590309 | 5/1981 | United Kingdom . |

*Primary Examiner*—P. E. Konopka
*Attorney, Agent, or Firm*—Keil & Weinkauf

[57] ABSTRACT

Molded catalyst materials contain metallic cobalt and-/or nickel particles and a lubricant, the said particles being obtained by reduction of cobalt oxide and/or nickel oxide particles containing less than 0.1% by weight of alkali metal oxides and/or alkaline earth metal oxides at $\leq 500°$ C., and the molded catalyst material having an indentation hardness greater than 300 kp/cm².

5 Claims, No Drawings

MOLDED CATALYST MATERIALS CONTAINING REDUCED COBALT AND/OR NICKEL PARTICLES

The present invention relates to molded catalyst materials containing metallic cobalt and/or nickel particles and a lubricant, and their preparation.

In the preparation of amines by hydrogenation of nitriles, e.g. hexamethylenediamine from adiponitrile, cobalt-containing catalysts are preferably used because their high selectivity. Such processes are disclosed in, for example, German Patent Nos. 1,072,972 and 1,259,899. However, the life of the cobalt catalysts used does not meet the technical requirements. The catalysts used have the disadvantage that they decompose during use, with the result that their mode of action is adversely affected. French Patent No. 1,407,414 also discloses that cobalt catalysts which are prepared by pressing cobalt oxide with graphite are used for the hydrogenation of adiponitrile to hexamethylenediamine. During use, such catalysts rapidly lose their hardness and disintegrate, with the result that their life is very restricted. German Laid-Open Application DOS No. 2,654,028 also discloses molded catalyst materials which contain metallic cobalt, alkali metal oxides, alkaline earth metal oxides and graphite. In the hydrogenation of adipodinitrile, however, these catalysts result in the formation of larger amounts of cyclic products.

It is an object of the present invention to provide molded catalyst materials containing cobalt and/or nickel, which have high activity, a long life and in particular great indentation hardness, mechanical stability and abrasion resistance.

We have found that this object is achieved by molded catalyst materials containing metallic cobalt and/or nickel particles and a lubricant, wherein the said metallic particles are obtained by reduction of cobalt oxide and/or nickel oxide particles containing less than 0.1% by weight of alkali metal oxides and/or alkaline earth metal oxides, at $\leq 500°$ C., and the molded catalyst materials have an indentation hardness greater than 300 kp/cm$^2$.

The present invention furthermore relates to a process for the preparation of molded catalyst materials by reduction of cobalt oxide and/or nickel oxide, wherein (a) cobalt oxide and/or nickel oxide particles are reduced by treatment with hydrogen at from 250° to 500° C. to give metallic cobalt and/or nickel particles, (b) the metallic cobalt and/or nickel particles are passivated by treatment with an inert gas containing molecular oxygen, (c) the passivated cobalt and/or nickel particles are pressed together with a lubricant to give moldings and, (d) the moldings containing the passivated cobalt and/or nickel particles and the lubricant are activated by treatment with hydrogen at from 250° to 500° C.

The present invention furthermore relates to the use of the molded catalyst materials containing metallic cobalt and/or nickel particles for the hydrogenation of organic compounds.

The said novel catalyst materials possess great indentation hardness and a long life and furthermore exhibit superior mechanical properties even after prolonged use. The novel catalysts furthermore have the advantage that they do not disintegrate, exhibit little abrasion, and still have a high selectivity even after they have been used for a long time.

The catalyst materials according to the invention contain metallic cobalt and/or nickel particles obtained from cobalt oxide and/or nickel oxide particles by contact with hydrogen at $=500°$ C. Advantageously, the metallic cobalt and/or nickel particles have a degree of reduction greater than 80%, in particular greater than 95%. The degree of reduction is the proportion, expressed as a percentage, of available cobalt and/or nickel present in metallic form. Advantageously, the content of alkali metal oxides and/or alkaline earth metal oxides is less than 0.1% by weight.

The novel catalyst materials furthermore contain a lubricant, for example an inorganic substance having a framework structure, such as talc or graphite. The catalysts advantageously contain the lubricant in an amount of from 1 to 5% by weight, based on the total catalyst material consisting of the active material, containing metallic cobalt and/or nickel particles, and the lubricant. Graphite has proven a particularly useful lubricant.

The novel catalyst material has an indentation hardness greater than 300, in particular from 350 to 1500, kp/cm$^2$.

Cobalt oxide and/or nickel oxide particles having a particle size of from 0.1 to 5, in particular from 0.2 to 2, $\mu$m are preferably used. The cobalt oxide and/or nickel oxide particles used as starting materials can contain other activating additives, such as manganese oxide, chromium oxide and/or copper oxide and pyrophosphoric and/or polyphosphoric acid. The oxide particles preferably contain from 80 to 99% by weight of nickel and/or cobalt in the form of their oxides, from 0.5 to 10% by weight of manganese, chromium and/or copper in the form of their oxides, the percentages being calculated as metal, and from 0.5 to 10% by weight of polyphosphoric and/or pyrophosphoric acid. Of course, the resulting active catalytic material without the lubricant has the appropriate composition for the ready-prepared catalyst. It is to be assumed that copper is present in the ready-prepared catalyst in the form of the metal, while the form in which manganese and/or chromium are present in the said catalyst is unknown.

The ready-prepared catalysts therefore essentially consist of metallic cobalt and/or nickel particles and small amounts of cobalt oxide and/or nickel oxide, depending on the degree of reduction, with or without the above additives, and a lubricant.

The novel catalyst materials are molded, for example in the form of spheres, tablets or extrudates.

In the preparation of the oxide particles, aqueous solutions of cobalt and/or nickel salts are, as a rule, used as starting materials. Where activating additives, such as manganese, chromium and/or copper, are to be used concomitantly, aqueous solutions of salts of these metals are used in addition. Examples of suitable salts are nitrates, sulfates, chlorides or salts with lower fatty acids. If the catalyst is intended to contain pyro phosphoric or polyphosphoric acid, phosphoric acid is concomitantly used, this being converted to pyrophosphoric or polyphosphoric acid during further processing. The starting solutions are advantageously first combined under acidic conditions, e.g. at a pH of from 1 to 2. As a rule, a mixture of the metal oxides, hydroxides and carbonates together with the acid components is then precipitated by means of aqueous alkali metal hydroxide solution, in particular a 10–25% strength by weight solution of this type, or aqueous alkali metal carbonate solution, in particular a 5–25% strength by weight solution of this type. It is also possible to allow the aqueous solutions of the metal compounds to run into the alkaline precipitating solution. It has proven advantageous to choose the ratio of acidic solution to alkaline precipitating agent so that the final pH of the reaction mixture is from 7.0 to 7.5. The precipitated mixture of oxides, hydroxides and/or carbonates is filtered off, washed free from foreign salts with water and dried. The mixture is then converted to the corresponding oxides by heating, temperatures of from 250° to 500° C. generally being sufficient for this purpose. As stated above, material obtained in this manner is, for example, then milled to a suitable particle size. In an advantageous procedure, the oxide material is made into a paste, for example with water, and then extruded, and the moldings obtained in this manner are once again heated at from 300° to 800° C. and then milled to the stated particle size. The resulting particles containing cobalt oxide and/or nickel oxide contain less than 0.1% by weight of alkali metal oxides and/or alkaline earth metal oxides.

The particles containing cobalt oxide and/or nickel oxide are reduced with hydrogen, for example in a fluidized bed, in a rotary tubular furnace or, preferably, in an agitated fixed bed, at from 250° to 500° C., in particular from 300° to 450° C., for example in the course of from 3 to 36 hours. It is advantageous to use a dry stream of hydrogen which is free of significant amounts of water, a relatively high hydrogen flow rate being maintained. It has proven useful to use not less than a 60-fold excess of hydrogen. Advantageously, the reduction is carried out until the degree of reduction is greater than or equal to 80%, in particular greater than or equal to 95%.

The metal particles are then stabilized by passivation. This procedure comprises the coating of the metal particles with an oxide layer by controlled oxidation, in order to eliminate the pyrophoricity due to the large free surface area of the small particles. This is achieved by treatment with an inert gas containing molecular oxygen. Advantageously, from 0.1 to 1.0 vol % of an inert gas containing molecular oxygen is used for this purpose, examples of inert gases being nitrogen and noble gases. It has proven particularly useful to employ an air/nitrogen mixture. The passivation is achieved by, for example, passing an air/nitrogen mixture over the metal powder, while exactly maintaining the temperature at a value which preferably does not exceed 100° C., in particular 80° C. After the stabilization, the degree of reduction should be no lower than 80%, preferably no lower than 90%. The stabilized cobalt and/or nickel particles have a diameter of from 0.05 to 2 μm, in particular from 0.2 to 1.2 μm.

The metallic cobalt and/or nickel particles passivated in this manner are mixed with an inert lubricant, preferably graphite. The lubricant is advantageously used in an amount of from 1 to 5% by weight, based on the sum of material containing metal particles and the lubricant. The mixture of passivated cobalt and/or nickel particles and lubricant is advantageously converted to moldings, e.g. pressed to give tablets, under a nitrogen atmosphere. The indentation hardness of the moldings is advantageously $\geq 300$ kp/cm$^2$. The moldings obtained in this manner are activated by treatment with a relatively large, e.g. 60-fold, excess of hydrogen in the absence of significant amounts of water, at $\leq 500°$ C., e.g. from 250° to 500° C., preferably from 300° to 360° C., under atmospheric or super-atmospheric pressure, e.g. from 100 to 150 bar. In this procedure, the degree of reduction reached should be, advantageously, higher than 95%. As a result of the activation, the indentation hardness of the moldings increases, for example from 300 to 600–800 kp/cm$^2$.

It has proven particularly useful if the ready-prepared activated molded catalyst material is again passivated, as described above, by treatment with an inert gas containing molecular oxygen, the degree of reduction not falling below 80%, and then activated again, as described above, by treatment with hydrogen at $\leq 500°$ C., preferably from 300° to 360° C., this process being repeated one or more times, advantageously from 1 to 5, in particular from 2 to 4, times. In this procedure, the indentation hardness increases with each cycle and reaches from 800 to 1300 kp/cm$^2$.

The novel catalyst materials possess high mechanical stability; this is achieved by producing the moldings together with lubricants not at the stage of the oxides but only after these have been reduced to cobalt and/or nickel particles and then passivated. If moldings which have been prepared from cobalt oxide and/or nickel oxide particles and lubricants and then activated are used, the indentation hardness of the moldings decreases, for example from 300 kp/cm$^2$ to <25 kp/cm$^2$, after the degree of reduction reaches 95%. The life of such catalysts is consequently substantially shortened.

The catalyst materials according to the invention can advantageously be used for the hydrogenation of organic compounds, in particular of olefinic double bonds or triple bonds, aldehyde, keto or carboxylic ester groups to the corresponding alcohols, or nitrile groups to the corresponding amines. They can also be used for the hydrogenation of alcohols, aldehydes or ketones, in the presence of ammonia, under aminating conditions to give the corresponding amines.

The novel catalyst can advantageously be used for the preparation of amines by hydrogenation of aliphatic, cycloaliphatic, araliphatic or aromatic nitriles of not more than 20 carbon atoms. The molecule may contain one or more nitrile groups. Compounds which are suitable for the hydrogenation are saturated or olefinically unsaturated nitriles. They may also possess substituents which are inert under the reaction conditions, e.g. alkyl radicals which have 1 to 4 carbon atoms and are bonded via ether bridges. Particularly preferred starting materials are alkanenitriles or alkanedinitriles of 3 to 18 carbon atoms. Examples of suitable nitriles are propionitrile, acetonitrile, acrylonitrile, benzyl cyanide, benzonitrile, glutarodinitrile, but-2-ene-1,4-dinitrile and adipodinitrile. The process has become particularly important industrially for the hydrogenation of adipodinitrile to hexamethylenediamine. The reaction is carried out in general under from 150 to 400, preferably from 200 to 300, bar and preferably at from 80° to 140° C., in particular from 100° to 120° C., in the presence of ammonia. It has proven useful for the volume ratio of nitrile to ammonia to be from 1:2 to 1:20, preferably from 1:6 to 1:12. It is also possible to replace some of the ammonia by recycled crude hydrogenation mixture, which essentially consists of amine and ammonia.

The novel molded catalyst materials are also suitable for the preparation of alcohols by hydrogenation of aldehydes, ketones or carboxylic esters. Preferably used starting materials are aliphatic, cycloaliphatic, araliphatic or aromatic aldehydes or ketones and carboxylic esters ($C_1$–$C_4$-alkanols) of not more than 20 carbon atoms. The molecule may contain one or more carbonyl or carboxylic ester groups. Compounds which are suitable for the hydrogenation are saturated or olefinically unsaturated aldehydes, ketones and carboxylic esters. They may also possess substituents which are inert under the reaction conditions, e.g. alkyl radicals which have 1 to 4 carbon atoms and are bonded via ether bridges, or aromatically bonded halogen atoms. Examples of suitable aldehydes are acetaldehyde, propionaldehyde, hexanal, octanal, decanal, 2-ethylhex-2-en-1-al, benzaldehyde, 2-phenylacetaldehyde, parachlorobenzaldehyde, acetophenone, methyl decyl ketone, isobutyraldehyde, 2-ethylhexanal and 2-ethyl-2-methylpent-2-en-1-al; oxo reaction mixtures which, in addition to butyraldehydes, contain by-products produced in the oxo reaction, e.g. acetals, esters and ethers, can also be used. Typical mixtures contain, for example, from 4 to 80% by weight of butyraldehyde, from 10 to 55% by weight of butanols, from 3 to 10% by weight of $C_1$–$C_4$-carboxylic esters, from 0.1 to 2% by weight of acetals and from 0.2 to 1% by weight of ethers and ketones. Aldehyde mixtures as obtained in the hydroformylation of olefin cuts containing $C_8$–$C_{10}$-olefins or $C_{10}$–$C_{12}$-olefins are also suitable. Of particular industrial importance is the hydrogenation of 2-ethyl-hex-2-en-1-al or aldehydes which are prepared directly by means of an oxo reaction of olefins with carbon monoxide and hydrogen. The novel catalyst is also suitable for the hydrogenation of alkanedicarboxylic ester mixtures to the corresponding alkanediols. The hydrogenation is carried out in general under from 30 to 300, in particular from 30 to 300, bar, and advantageously at from 80° to 200° C., in particular from 100° to 180° C.

The Examples which follow illustrate the invention.

EXAMPLE 1

4480 g of cobalt nitrate, $Co(NO_3)_2 \times 6H_2O$, 261 g of manganese nitrate, $Mn(No_3)_2 \cdot 6H_2O$, and 47 g of 85% strength by weight phosphoric acid are dissolved in 10 liters of water, and this solution is run slowly into a stirred solution of 1900 g of sodium carbonate, $Na_2CO_3$, in 10 liters of water. When the addition of the metal salt solution is complete, the pH of the mixture has fallen to 7.0. The mixture is cooled, and the precipitate is then filtered off under suction and washed with water until it is free of sodium ions. The filter cake is dried and then heated at 300° C. until the material is free of carbonate. The oxide mixture is then made into a paste with sufficient water to produce a kneadable mass, which is converted to extrudates. The extrudates are then heated at 450° C. for 24 hours in a muffle furnace, and the resulting extrudates are milled to give particles having a size of from 0.1 to 1.2 μm.

600 kg of the cobalt oxide-containing particles prepared in this manner are reduced to metallic cobalt in an agitated fixed bed at 400° C. for 38 hours with 400 $m^3$(S.T.P.)/h of hydrogen, the degree of reduction being greater than 95%, based on cobalt (stoichiometric excess of hydrogen: 64). The pyrophoric metal pigment is then coated with a stabilizing oxide layer, and thus passivated, in a nitrogen/air mixture at 60° C.; the degree of reduction should not fall below 90%.

To produce moldings having a diameter of 5 mm and a height of 4 mm, the passivated pulverulent metal pigment is mixed with 2% by weight of graphite, and the mixture is tabletted under a nitrogen atmosphere. The indentation hardness of the tablets is 300 kp/$cm^2$.

In a high pressure vessel, 350 liters of the moldings produced in this manner are treated with a large excess of hydrogen at 360° C. and under 150 bar for 24 hours in order to activate them. The hydrogen is circulated via a condenser in order to separate off the water of reduction. The resulting molded catalyst material has a degree of reduction of 98% and an indentation hardness of 620 kp/$cm^2$ It is then passivated by treatment with a mixture of nitrogen and air containing 0.5 vol % of oxygen, at 60° C., the degree of reduction not falling below 90%. Thereafter, the molded catalyst material is again activated with hydrogen at 360° C. and under 150 bar, as described above. The moldings thus obtained have an indentation hardness of 950 kp/$cm^2$. After the passivation/activation cycle has been repeated a second time, the moldings have an indentation hardness of 1140 kp/$cm^2$.

After the catalyst has been cooled, the reaction vessel is charged, by a trickle-bed procedure and under a hydrogen pressure of 270 bar, with a mixture of 85 liters/hour of adipodinitrile, 255 liters/hour of liquid ammonia and 850 liters/hour of crude hydrogenation mixture, the hydrogen being circulated (400 $m^3$(S.T.P.)/h). The temperature of the feed mixture is 65° C., and that of the reactor exit is 95° C. The maximum hot spot temperature which results is 100° C. Analysis of the crude hexamethylenediamine by gas chromatography after the ammonia has been evaporated from the hydrogenation mixture gives 0.02% by weight of hexylamine, 0.05% by weight of azacycloheptane, 0.06% by weight of 1,2-diaminocyclohexane, 0.003% by weight of 2-aminomethylcyclopentylamine and 99.36% by weight of hexamethylenediamine, as well as an aminocapronitrile content of <0.01% by weight. The distillation residue predominantly consists of bishexamethylenetriamine and amounts to 0.3% by weight. This gives a selectivity of 99.5% with respect to hexamethylenediamine. After a time-on-stream of 520 days, the catalyst has constant activity and selectivity, without any regeneration. At the end of this time, the molded catalyst material has an indentation hardness of >900 kp/$cm^2$.

COMPARATIVE EXAMPLE 1

The cobalt oxide prepared as described in Example 1 is mixed with 2% of graphite, and the mixture is pressed to give tablets (diameter 5 mm, height 4 mm). The indentation hardness is adjusted to 300 kp/$cm^2$, and the tablets are then brought to a degree of reduction of ≧95% with hydrogen at 360° C. As a result of the reduction of the cobalt oxide, the indentation hardness of the tablets falls sharply to ≦25 kp/$cm^2$. Contact with the lateral surface of the cylinder readily causes the tablets to disintegrate into disks.

In contrast to tablets produced from cobalt oxide which has already been reduced to cobalt, the mechanical stability of these tablets cannot be improved by repeated passivation and reduction.

COMPARATIVE EXAMPLE 2

A high pressure vessel having a length of 2 m and a diameter of 42 mm is charged with 3 liters of a passivated cobalt catalyst prepared as described in Example 1 of German Laid-Open Application DOS No. 2,654,028. The catalyst contains 1.5% by weight of calcium oxide and 2.7% by weight of sodium salts, calculated as sodium oxide. The catalyst is activated by heating at 330° C. in a stream of hydrogen.

After the cooling process, the high pressure vessel is charged, by a trickle-bed procedure and under a hydrogen pressure of 270 bar, with 0.4 liters/hour of adipodinitrile, 1.2 liters/hour of liquid ammonia and 4.5 liters/hour of crude hydrogenation mixture, the temperature in this procedure being kept at 140° C. Analysis of the crude hexamethylenediamine by gas chromatography after the ammonia has been evaporated from the hydrogenation mixture gives 99.69% by weight of hexamethylenediamine, 0.06% by weight of 1,2-diaminocyclohexane and 0.12% by weight of 2-aminocyclopentylamine.

We claim:

1. A molded catalyst material containing metallic cobalt and/or nickel particles and from 1 to 5% by weight of graphite, wherein the said metallic particles are obtained by reduction of cobalt oxide and/or nickel oxide particles having particle size of from 0.1 to 5 μm and containing less than 0.1% by weight of alkali metal oxides and/or alkaline earth metal oxides, at ≦500° C. to a degree of reduction greater than 95% and the molded catalyst material has an indentation hardness greater than 300 kp/cm².

2. A molded catalyst material as claimed in claim 1, having an indentation hardness of from 350 to 1500 kp/cm².

3. A molded catalyst material as claimed in claim 1, which additionally contains manganese, chromium and/or copper.

4. A molded catalyst material as claimed in claim 1, which additionally contains pyrophosphoric and/or polyphosphoric acid.

5. A process for the preparation of a molded catalyst material wherein (a) cobalt oxide and/or nickel oxide particles having a particle size of from 0.1 to 5 μm and containing less than 0.1% by weight of alkali metal oxides and/or alkaline earth metal oxides are reduced by treatment with hydrogen at from 250° to 500° C. to give metallic cobalt and/or nickel particles having a degree of reduction greater than 95%, (b) the metallic cobalt and/or nickel particles are passivated by treatment with an inert gas containing from 0.1 to 1.0% by volume of molecular oxygen, while maintaining a temperature of not more than 100° C. and achieving a degree of reduction of not less than 80%, (c) the passivated cobalt and/or nickel particles are pressed together with 1 to 5% by weight of graphite to give moldings and (d) the moldings containing the passivated cobalt and/or nickel particles and graphite are activated by treatment with hydrogen at from 250° to 500° C., achieving a degree of reduction ≧95%, and (e) the moldings containing cobalt and/or nickel particles and graphite are again passivated by treatment with an inert gas containing from 0.1 to 1% by volume of molecular oxygen while maintaining a temperature of not more than 100° C. and achieving a degree of reduction of not less than 80% and then activated by treatment with hydrogen at from 250° to 500° C., achieving a degree of reduction ≧95%, these procedures being carried out from 1 to 5 times, and achieving a molded catalyst material having an indentation hardness of from 800 to 1300 kp/cm².

* * * * *